United States Patent
Anglada

(10) Patent No.: US 9,498,368 B2
(45) Date of Patent: Nov. 22, 2016

(54) DEVICE FOR GRIPPING THE FOREARM OF A USER SUFFERING FROM MUSCULAR PROBLEMS IN THE ELBOW

(75) Inventor: Gerard Anglada, Saint Etienne (FR)

(73) Assignee: GIBAUD, Saint Etienne (FR)

( * ) Notice: Subject to any disclaimer, the term of this patent is extended or adjusted under 35 U.S.C. 154(b) by 994 days.

(21) Appl. No.: 12/526,082

(22) PCT Filed: Feb. 7, 2008

(86) PCT No.: PCT/FR2008/000146
§ 371 (c)(1),
(2), (4) Date: Oct. 7, 2009

(87) PCT Pub. No.: WO2008/110702
PCT Pub. Date: Sep. 18, 2008

(65) Prior Publication Data
US 2010/0042031 A1    Feb. 18, 2010

(30) Foreign Application Priority Data
Feb. 15, 2007   (FR) ...................................... 07 01113

(51) Int. Cl.
*A61F 5/30*  (2006.01)
*A61F 13/10*  (2006.01)

(52) U.S. Cl.
CPC ............... *A61F 5/30* (2013.01); *A61F 13/102* (2013.01)

(58) Field of Classification Search
USPC ......... 602/20–22, 5–6, 63–64; 128/875–876, 128/878–881; 2/20, 16, 158–160, 161.6
See application file for complete search history.

(56) References Cited

U.S. PATENT DOCUMENTS

| | | | | | |
|---|---|---|---|---|---|
| 3,757,807 | A | * | 9/1973 | Manzo | A61H 3/0288 135/68 |
| 5,145,179 | A | * | 9/1992 | Breed | A63B 69/0059 273/DIG. 30 |
| 5,441,058 | A | * | 8/1995 | Fareed | 128/898 |
| 5,468,220 | A | * | 11/1995 | Sucher | 602/21 |
| 5,642,739 | A | | 7/1997 | Fareed | |
| 5,672,150 | A | | 9/1997 | Cox | |
| 6,077,241 | A | * | 6/2000 | Fareed | 602/62 |
| 6,085,765 | A | * | 7/2000 | Sigsworth | A61H 3/02 128/878 |

(Continued)

OTHER PUBLICATIONS

Written Opinion in International Patent Application No. PCT/FR2008/000146 filing date Feb. 7, 2008.

*Primary Examiner* — Ophelia A Hawthorne
(74) *Attorney, Agent, or Firm* — Workman Nydegger

(57) ABSTRACT

A device is provided for gripping the forearm of a user suffering from muscular problems in the elbow. The device defines a rigid but elastically deformable U-shaped body, and has a bottom. The device includes a first limb and a second limb, and two supporting elements which are mounted on the body such that each one is essentially located on a free end part of a limb of the body. One of the limbs of the body defines a first curved part which is adjacent to the bottom wherein the concave region of the curved part is oriented towards the inside of the body, and a second curved part which extends from the first part towards the free end of the limb. The concave region of the second part is oriented towards the outside of the body such that the limb of the U has a transversal flexion line.

18 Claims, 2 Drawing Sheets

(56) References Cited

U.S. PATENT DOCUMENTS

| | | | |
|---|---|---|---|
| 6,120,472 A * | 9/2000 | Singer, Jr. | 602/64 |
| 6,361,549 B1 * | 3/2002 | Asatourian et al. | 606/204 |
| 6,398,749 B1 * | 6/2002 | Slautterback | 602/62 |
| 6,540,710 B1 * | 4/2003 | Cruz | 602/21 |
| 2002/0062095 A1 * | 5/2002 | Slautterback | 602/21 |
| 2003/0018286 A1 * | 1/2003 | Porrata | A61F 5/0118 602/21 |
| 2003/0093017 A1 * | 5/2003 | Loud | A61F 5/0118 602/2 |
| 2003/0130604 A1 * | 7/2003 | Porrata et al. | 602/21 |
| 2006/0118679 A1 * | 6/2006 | Delgado et al. | 248/118 |

* cited by examiner

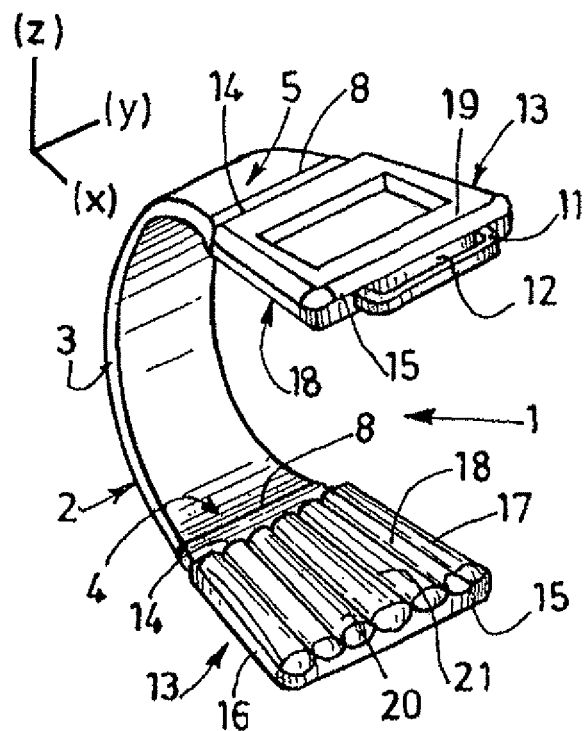
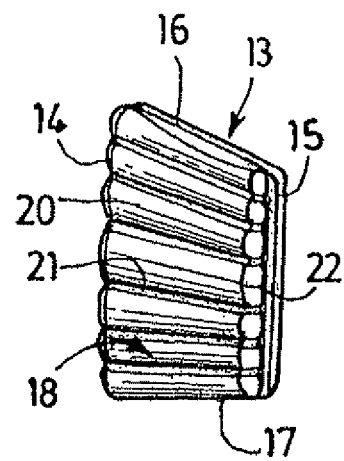
FIG. 1
FIG. 4
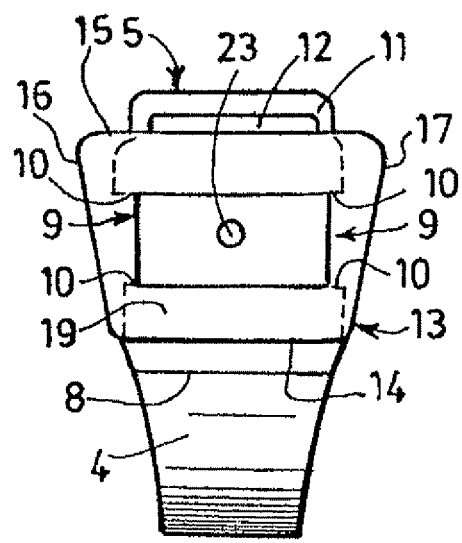
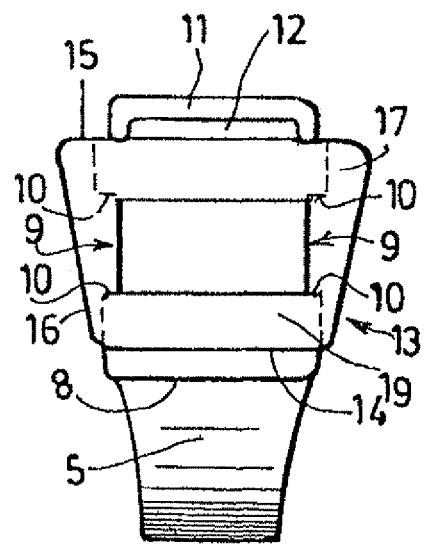
FIG. 2
FIG. 3

DEVICE FOR GRIPPING THE FOREARM OF A USER SUFFERING FROM MUSCULAR PROBLEMS IN THE ELBOW

FIELD OF THE INVENTION

The present invention relates to a gripping device intended to be placed around the forearm of a user, for preventing or alleviating muscular problems of the elbow.

BACKGROUND

Muscular problems more specifically targeted by the present invention are epicondylitis and epitrochleitis. These are two types of tendonitis which are expressed by pain in the elbow and are often due to too large straining of the forearm muscles. These problems may notably appear as a result of repetitive, poorly performed or particularly hard movements of the hand and/or of the wrist, whether this be while working (carpenters, masons, pneumatic drill operators, etc.) or while practicing sports (tennis, golf, etc.) or during leisure (for example gardening).

Epicondylitis occurs when the tendon of the extensor muscles is strained too much; the pain is then especially located in the external part of the forearm, in the region of the epicondyl, which is a small bone protrusion of the external face of the humerus.

Epitrochleitis, which is much less frequent, occurs when the tendon of the flexor muscles attached to the epitrochlea (a small bone protrusion of the internal face of the humerus) is overused; the pain is then located in the internal region of the forearm, in the region of the epitrochlea.

Both of these disorders cause pain which may last for a few weeks, or even be further prolonged, and if they are poorly treated, they may degenerate into chronic pain and cause irreversible lesions.

If it is preferable at the beginning of the attack, to rest the elbow, by avoiding gestures which have caused the lesion, on the other hand, prolonged immobilization should be banned since this risks causing serious stiffness of the joint, which is sometimes irreversible. Next, in the re-adaptation phase, when the movements are gradually resumed, wearing a device for gripping the forearm may be advised, which allows limitation of the straining experienced by the tendon by locally compressing the muscle. Such a gripping device may also be used preventively, so as to be continually worn during the risky activity.

Such gripping means which typically comprise a stiff but elastically deformable body having substantially the shape of a U, having a bottom and first and second limbs, on the one hand, and two supporting members each substantially mounted on the body to a free utmost portion of a limb of the latter on the other hand are already known.

The user places the body of the device around his/her forearm in the suitable region, and then tightens it by means of a strap. The supporting members will then locally compress the forearm, thereby limiting the amplitude of the movement of the tendon.

These known devices however have a certain number of drawbacks.

First of all, obtaining satisfactory tightening at the supporting members is generally accompanied by too significant tightening at the other contact areas between the body and the forearm. The result is a tourniquet effect, which may lead to failure of vascularization, which of course is not desirable.

Moreover, the known devices are often difficult to set into place, because the body may rotate around the forearm during the tightening with the strap, and may finally be in a bad position. Further, it should be noted that epicondylitis and epitrochleitis generally occur on the elbow of the right arm for a right-handed person, and of the left arm for a left-handed person, so that the setting into place of the body is achieved with the left hand for a right-handed person and with the right hand for a left-handed person. This further complicates the placement of the device by a user alone.

Further, the supporting members of certain known devices have an effective supporting area with reduced dimensions. This may be detrimental to the effectiveness of the device which does not provide satisfactory compression of the forearm in the suitable area, but this may also lead to intensification of the tourniquet effect.

Moreover, devices for supporting the wrist are known. Thus, document US 2006/118679 proposes a device which includes a flat body embedded in a flexible sheath provided with a cavity positioned under the carpal tunnel. The standard shape of the body, as a C, induces the drawbacks described above relating to the tourniquet effect. As for document U.S. Pat. No. 5,672,150, it describes a device which includes an upper portion and a lower portion placed above and below the wrist respectively, these portions being clasped by a strap so as to be brought closer to each other. This application is relatively difficult.

SUMMARY

The present invention aims at finding a remedy to the aforementioned drawbacks.

For this purpose, the invention relates to a gripping device of the aforementioned type, wherein at least one of the limbs of the body includes a first curved portion, adjacent to the bottom of the U, the concavity of which is oriented towards the inside of the body, and a second curved portion extending the first portion towards the free end of the limb, the concavity of which is oriented towards the outside of the body, so that said limb of the U has a transverse inflection line.

The term "transverse" designates the direction orthogonal to the general direction in which extends the limb of the U, and substantially contained in the average plane defined by the limb. In other words, the transverse direction corresponds to the general direction of the forearm equipped with such a gripping device.

With this inflection line, the relevant limb of the body thus has the shape of the limb of an arc. By means of this structure, when the device is placed on the forearm of a user and tightened with a strap, large amplitude tightening is obtained at the supporting members, which are oriented towards the inside of the U-shaped body and located facing each other. By this tightening of the forearm between the supporting members of the device, the desired compression of the muscle of the forearm may be achieved, while the tightening force on the forearm at the other areas is limited. Thus, the tourniquet effect is avoided. Further, it is not necessary for the user to significantly tighten the device in order to obtain localized compression of the muscle with a satisfactory amplitude, because of the dual curvature of the limb(s) producing a "lever arm" effect.

Moreover, because of this structure of the body, the second curved portion of the relevant limb moves away from the other limb when one moves away from the bottom of the U. Thus, the U has a flared opening which facilitates insertion of the forearm and therefore placement of the body.

Advantageously, it may be provided that each of the two limbs of the body includes a first curved portion, adjacent to the bottom of the U, the concavity of which is oriented towards the inside of the body and a second curved portion, extending the first portion towards the free end of the limb, the concavity of which is oriented towards the outside of the body, so that each of the two limbs of the U have a transverse inflection line. The aforementioned advantages are thus further increased.

Said or each inflection line is for example substantially located in the middle of the limb.

According to a possible embodiment, the width of at least one limb increases from the bottom of the U towards the free end of said limb. The contact area between the forearm and the body in the suitable area may thereby be increased.

For example, at least one the supporting members includes an inner cavity in which the free utmost portion of the corresponding limb is housed, and the gripping device further includes means for holding the supporting member in position mounted on the body.

According to a first embodiment, these holding means comprise a rivet or any other attachment means. According to a second embodiment, these holding means comprises hooking means arranged on said free utmost portion, capable of retaining the supporting member in position mounted on the body. For example, this may be a hook which will cooperate with the inner face of the cavity. The supporting member may notably be fitted in between two shoulders provided on said free utmost portion.

At least one of the limbs may have at its free end a slot laid out in order to provide the passage for an attachment strap around the forearm of the user. Alternatively, the strap may pass into a cavity while being sandwiched between the body and the supporting member.

Advantageously, at least one of the supporting members may have, on its face turned towards the inside of the body, ribs substantially parallel with each other, and oriented longitudinally.

The longitudinal direction designates the general direction in which the limb of the U extends. In other words, the longitudinal direction is orthogonal to the fibers of the muscle of the forearm equipped with such a gripping device.

The effect associated with these ribs is to maximize the compressive force and to distribute it over a larger surface. This aims at increasing the effectiveness of tightening and allowing the user to reduce the pain felt.

The combination of these ribs with the presence of an inflection line on one or two limbs of the body leads to a particularly satisfactory gripping device, since it provides significant compression localized in the suitable area (at the supporting members) and minimizes the tourniquet effect in the other areas.

It should be noted that the second supporting member may include similar ribs in order to also play the role of a compressive member. Alternatively, this second member may simply play the role of a counter support. In this case, it may be smooth or include concentric ribs which aim at preventing or limiting rotation of the body around the forearm of the user.

At least one of the supporting members may substantially have a trapezium shape, the bases of which are oriented transversely, and which flares towards the free end of the limb on which it is mounted. Thus the supporting surface against the forearm may be increased. In addition to increasing the gripping effectiveness, with this geometry it is possible to obtain the expected effect, even if the user does not accurately position the device on his/her forearm.

Advantageously, at least one of the supporting members may be made in a material having anti-sliding properties, such as silicone or an elastomer, in order to avoid rotation of the body around the forearm of the user when the gripping device is set into place, but also during activities, possibly abrupt activities, of the user (squash, use of a pneumatic drill, etc.). The device is preferably worn directly on the body and not over clothes.

BRIEF DESCRIPTION OF THE DRAWINGS

A possible embodiment of the invention is now described as a non-limiting example with reference to the appended drawings:

FIG. 1 is a perspective view of the gripping device according to the invention;

FIGS. 2 and 3 are side views from two opposite sides of the device of FIG. 1;

FIG. 4 is a perspective view of a supporting member;

DETAILED DESCRIPTION OF VARIOUS EMBODIMENTS

A gripping device 1 first of all comprises a substantially U-shaped body 2 having a bottom 3 as well as first and second limbs 4, 5. The body 2 is made in a stiff material by which the desired tightening may be generated, but in an elastically deformable material, so that the limbs may be slightly moved apart upon inserting the forearm into the body 2 on the one hand, and so that on the other hand the limbs may be bent towards each other upon tightening the body 2 with a strap. Among the materials which are suitable, mention may be made of polypropylene, polyamide. The thickness of the body is for example comprised between 2 and 3 mm. The body 2 may be made by injection.

Figure 5:
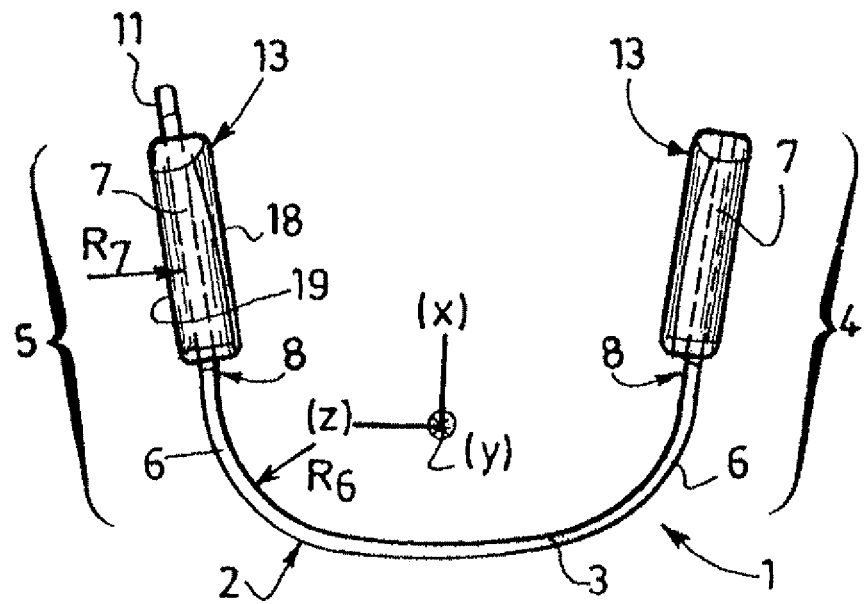
FIG. 5 is a front view of the device of FIG. 1.

As illustrated in FIGS. 1 and 5, the longitudinal direction (x) is defined as the general direction in which the limbs of the U extend and the transverse direction (y) as the direction orthogonal to the longitudinal direction and substantially parallel to the average planes of the limbs 4, 5 and of the bottom 3 of the U. The direction (z) is also defined as the direction orthogonal to (x) and (y).

The bottom 3 of the U is rounded; it may have a variable dimension along (z) depending on the size and build of the user, comprised between 7 and about 9 cm. A device of large size is illustrated in the figures, having a bottom 3 including a relatively planar central portion, while on smaller devices, the bottom 3 more and more similar to a circular arc.

Each of both limbs 4, 5 include a first curved portion 6 adjacent to the bottom 3 of the U, the concavity of which is oriented towards the inside of the body 2 and a second curved portion 7 extending the first portion 6 as far as the free end of the limb, the concavity of which is oriented towards the outside of the body 2. The radius of curvature $R_6$ of the first portion 6 is comprised between 2 and 4 cm, for example of the order of 2.8 cm; the radius of curvature $R_7$ of the second portion 7 is much larger, for example comprised between 9 and 11 cm.

Thus, between the first and the second portions 6, 7 a transverse inflection line 8 is formed and each limb 4, 5 has the shape of an arc limb. In the illustrated embodiment the transverse inflection line 8 is substantially located in the middle of each limb 4, 5.

The width (along the transverse direction) of the body 2 is of the order of 3 cm at the bottom 3 and then gradually increases when one moves towards the free ends of the limbs 4, 5 until it attains about 4 cm in the vicinity of the inflection line 8, and remains constant in the second portion 7 of each limb.

The first limb 4 (FIG. 2) includes two side recesses 9 at its utmost portion, which form on either side of the limb 4 (along the transverse direction) two shoulders 10. The second limb 5 (FIG. 3) has a similar shape and further includes an extension 11 provided with a slot 12 oriented transversely, extending over about 3 cm.

The gripping device 1 further comprises two supporting members 13 as more specifically illustrated in FIG. 4. Each supporting member 13 has a general trapezium shape including a large base 14, a small base 15 and two sides 16, 17, symmetrical relatively to a perpendicular to the bases 14, 15. As an example, the size of the large base 14 may be of the order of 55-60 cm, and that of the small base 15 of the order of 42-50 cm; the distance between both bases 14, 15 may be of the order of 4.5-5.5 cm.

Each supporting member 13 also has two main faces, i.e. an inner face 18 and an outer face 19. The inner face 18 is provided with ribs 20 substantially parallel with each other and perpendicular to the bases 14, 15. The ribs 20 here assume the shape of elongated bosses, without any sharp edges. Grooves 21 are defined between two ribs 20.

In each supporting member 13, an inner cavity 22 is formed substantially parallel to the main faces 18, 19, opening out at least into the small base 15 as well as on the outer face 19 but not on the inner face 18.

The supporting members 13 are made in a material having anti-sliding properties, such as silicone or an elastomer. They are each mounted on a free utmost portion of a limb 4, 5 of the body 2 of the device, this utmost portion being engaged into the cavity 22 from the small base 15, and the inner face 18 being turned towards the opposite limb, i.e. towards the inside of the body 2. The supporting members 13 are fitted in between both shoulders 10.

The supporting member 13 mounted on the first limb 4 is attached to the latter by a rivet 23. The supporting member 13 mounted on the second limb 5 is crossed by the latter so that the extension 11 provided with the slot 12 protrudes from the supporting member 13.

A strap 24 completes the gripping device 1. The strap 24 for example includes two main faces provided with fastening means of the VELCRO® type. This strap 24 is inserted into the cavity 21 of the supporting member mounted on the first limb 4, outside the body 2, runs along on the outer side the first limb 4, the bottom 3 and the second limb 5, and then passes into the slot 12.

Figure 6:
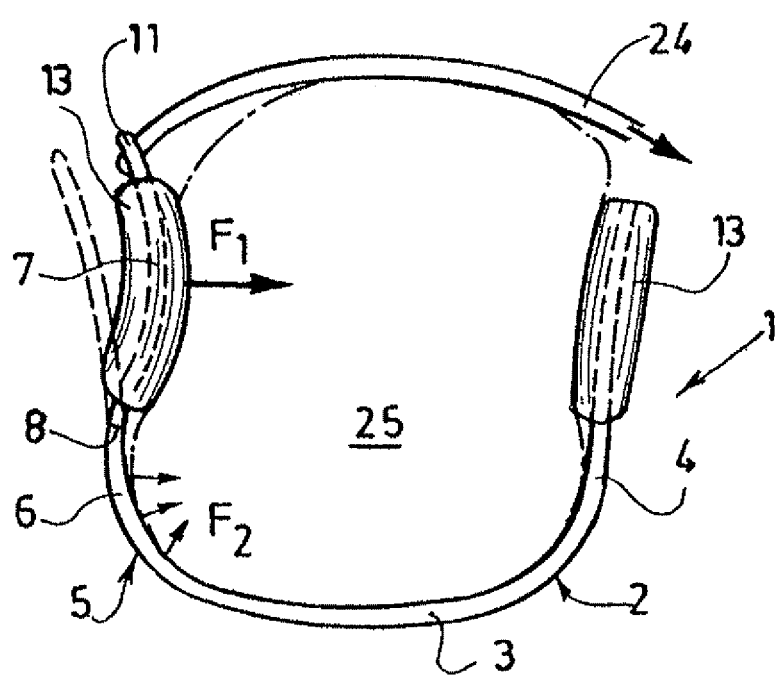
FIG. 6 schematically illustrates the device set into place and tightened around the forearm of a user.

Upon tightening the device 1 on the forearm 25 of a user (FIG. 6), the limbs 4, 5 are elastically deformed and brought closer to each other. For example, the second limb 5 is substantially subject to pivoting of its second portion 7 relatively to its first portion 6 around the inflection line 8. Thus, the arc limb shape of the second limb 5 is enhanced, the limb assuming the shape of a flattened S.

Accordingly, both limbs 4, 5 are brought closer together at the supporting members 13, and therefore significant tightening is obtained in the corresponding area of the forearm, symbolized by the arrow F1. On the other hand, in the other peripheral areas of the forearm, in particular at the first portion 6 of the limbs 4, 5 which have not been brought very close to each other, the tightening force F2 applied to the forearm is less, and the tourniquet effect is avoided. The pressure exerted on the forearm is therefore localized at the supporting members 13.

With the flared shape of the opening of the body and by bringing both limbs closer to each other during the tightening, nipping of the skin may also be avoided during the setting into place of the device 1.

As the supporting surface (inner face 18) is large, the user is not required to obtain very accurate positioning of the body 2, unlike with the devices from the prior art.

Generally, one of the supporting members plays the role of a means for compressing the muscle, and is placed on the suitable side of the forearm depending on the muscular problem to be prevented/alleviated. The ribs 20 of this supporting member 13 are oriented perpendicularly to the fibers of the muscle, which maximizes the compressive force. The other supporting member plays the role of a counter support and preferably of a means for preventing sliding. Therefore it is not necessarily provided with ribs perpendicular to the fibers of the muscle.

The device, existing in several sizes, is suitable for being placed on a left or right arm. Optionally, the body may include a visual mark on its outer face, such as a logo, in order to indicate to the user the proper direction for its placement. Indeed, a gripping device may be provided, for which both limbs of the body have substantially the same length and all have dual curvature. In this case, the gripping device substantially has a plane of symmetry, which is parallel to the general direction in which the limbs of the U extend and to the inflection line. The logo therefore facilitates the placement of the device in spite of this symmetry.

It is obvious that the invention is not limited to the embodiment described above as an example but that on the contrary, it encompasses all the alternative embodiments.

The invention claimed is:
1. A gripping device intended to be placed around a forearm of a user, for preventing or alleviating muscular problems in an elbow, comprising:
   a stiff and elastically deformable body substantially having a shape of a "U", having a bottom and a first limb and a second limb, and
   a first supporting member and a second supporting member, each being separate from one another, the first supporting member mounted only to a free utmost end portion of the first limb and the second supporting member substantially mounted only to a free utmost portion of the second limb, the first supporting member opposing the second supporting member on the first and second limbs, respectively,
   wherein each of the first limb and the second limb includes a first curved portion adjacent to the bottom of the U, and a second curved portion extending from the first curved portion to the free end of each limb,
   wherein in the first curved portion of each of the first limb and the second limb, a concavity is oriented towards an inside of the body, and in the second curved portion of each of the first limb and the second limb, a concavity is oriented towards an outside of the body, so that each of the first limb and the second limb of the "U" shape has a transverse inflection line such that the second curved portion of the first and second limbs each form an arc, at a location specified by the transverse inflection line, thereby enabling the gripping device to be placed on the forearm of the user and tightened with an attachment strap, such that large amplitude tightening is obtained at the first and second supporting members, which are oriented toward the inside of the U-shaped body.

2. The gripping device according to claim 1, wherein at least one of the supporting members is made of a material having anti-sliding properties.

3. The gripping device according to claim 2, wherein the anti-sliding material is selected from the group consisting of silicone and elastomeric materials.

4. The gripping device according to claim 1, wherein said transverse inflection line is substantially located in a middle of the limb.

5. The gripping device according to claim 1, wherein a width of at least one limb increases from the bottom of the U towards the free end of said limb.

6. The gripping device according to claim 1, wherein
at least one of the supporting members includes an inner cavity in which the free utmost portion of the corresponding limb is housed, and
the gripping device further includes an attachment mechanism configured to hold the supporting member in position mounted on the body.

7. The gripping device according to claim 1, wherein at least one of the limbs has at its free end a slot laid out in order to provide passage for the attachment strap around the forearm of the user.

8. The gripping device according to claim 1, wherein at least one of the supporting members has, on its face turned towards the inside of the body, ribs substantially parallel to each other and oriented longitudinally.

9. The gripping device according to claim 1, wherein at least one of the supporting members substantially has a trapezium shape, the bases of which are oriented transversely, and which flares towards the free end of the limb on which it is mounted.

10. A gripping device intended to be placed around a forearm of a user, for preventing or alleviating muscular problems in an elbow, comprising:
a stiff and elastically deformable body having a base portion with two ends, and two opposing limbs each connected to an end of the base portion through a curvature in each limb, the two opposing limbs extending outwardly away from a central longitudinal axis arranged perpendicular to the base portion; and
two supporting members each removably positioned only on a free end of each limb and separate from one another,
wherein the curvature in each of the two opposing limbs of the body includes a first curved portion adjacent to the base portion and a second curved portion extending from the first curved portion to the free end of the limb, and
wherein in the first curved portion of each of the two opposing limbs, a concavity is oriented towards an inside of the body, and in the second curved portion of each of the two opposing limbs, a concavity is oriented towards an outside of the body, so that each of the two opposing limbs has a transverse inflection line.

11. The gripping device according to claim 10, wherein each supporting member has an inner cavity and the free end of each limb engages the inner cavity of one of the supporting members.

12. The gripping device according to claim 10, wherein at least one of the supporting members is made of a material having anti-sliding properties.

13. The gripping device according to claim 10, wherein at least one of the supporting members is made of a silicone or an elastomer.

14. The gripping device according to claim 10, wherein at least one of the limbs has at the free end a slot through which an attachment strap is able to pass.

15. The gripping device according to claim 10, wherein at least one of the supporting members has ribs which are oriented longitudinally.

16. A gripping device intended to be placed around a forearm of a user, for preventing or alleviating muscular problems in an elbow, comprising:
a stiff and elastically deformable body having a substantially straight base portion with a first end and a second end and two opposing limbs, each of the two opposing limbs having an end portion;
two supporting members, one of the two supporting members only positioned on the end portion of one of the two opposing limbs and another of the two supporting members only positioned on the end portion of another of the two opposing limbs, the two supporting members being separate from one another;
wherein each of the two opposing limbs includes a curved portion that curves toward the opposing limb; and
wherein the end portion of at each of the limbs curves away from the opposing limb, so that each of the two opposing limbs has a transverse inflection line.

17. The gripping device according to claim 16, wherein the body is formed of polypropylene or polyamide.

18. The gripping device according to claim 16, wherein at least one of the supporting members is made of a material having anti-sliding properties.

* * * * *